United States Patent [19]

Ranken et al.

[11] Patent Number: 4,594,453

[45] Date of Patent: Jun. 10, 1986

[54] PROCESS FOR PREPARING (HYDROCARBYLTHIO)AROMATIC AMINES

[75] Inventors: Paul F. Ranken, Baton Rouge, La.; Bonnie G. McKinnie, Magnolia, Ark.

[73] Assignee: Ethyl Corporation, Richmond, Va.

[21] Appl. No.: 619,675

[22] Filed: Jun. 11, 1984

[51] Int. Cl.$^4$ ............................................. C07C 149/42
[52] U.S. Cl. ..................................... 564/440; 564/335; 564/430; 564/305; 564/307; 548/541; 548/543
[58] Field of Search ............... 564/440, 335, 430, 307, 564/305; 568/54; 548/541, 543

[56] References Cited

U.S. PATENT DOCUMENTS

| | | | |
|---|---|---|---|
| 1,940,757 | 12/1933 | Lehmann et al. | |
| 2,923,743 | 2/1960 | Delfs et al. | 568/38 |
| 3,272,814 | 9/1966 | Cutler et al. | 544/206 |
| 3,920,444 | 11/1975 | Harrington et al. | 71/103 |
| 4,146,688 | 3/1979 | Schwindt et al. | 521/159 |

OTHER PUBLICATIONS

Cadogan, J. I. G., "A Convenient New Method of Aromatic Arylation", J. of Chemical Society, 1962, pt. III, pp. 4257–4258.

Friedman, L. & Chlebowski, J. F., "Aprotic Diazotization of Arylamines", J. of Organic Chemistry, 1968; vol. 33, pp. 1633–1638.

Giam, C. S. & Kikukawa, K., "A Simple Preparation of Aromatic or Heteroaromatic Sulfides", in *Journal of the Chemical Society Chem. Commun.*, vol. 16 (1980) pp. 756–757.

Fieser and Fieser, Reagents for Organic Synthesis, John Wiley and Sons, New York, 1964, p. 41.

*Primary Examiner*—Charles F. Warren
*Assistant Examiner*—John A. Sopp
*Attorney, Agent, or Firm*—Donald L. Johnson; John F. Sieberth; Patricia J. Hogan

[57] ABSTRACT

(Hydrocarbylthio)aromatic amines are prepared by reacting an aromatic amine, such as an aminobenzene, with a hydrocarbyl disulfide, such as an alkyl disulfide. The reaction is preferably conducted in the presence of a Lewis acid catalyst, such as aluminum chloride.

11 Claims, No Drawings

PROCESS FOR PREPARING (HYDROCARBYLTHIO)AROMATIC AMINES

FIELD OF INVENTION

This invention relates to (hydrocarbylthio)aromatic amines and more particularly to a process for preparing them.

BACKGROUND

As indicated in U.S. Pat. No. 3,272,814 (Cutler et al.), U.S. Pat. Nos. 3,920,444 (Harrington et al.), and 4,146,688 (Schwindt et al.), it is known that various (hydrocarbylthio)aromatic amines are useful as intermediates in the preparation of biologically-active materials, polyurethanes, etc., and that they can be prepared by various techniques involving multi-step reactions. It is also known from U.S. Pat. No. 4,324,920 (McKinnie et al. I) and copending applications Ser. No. 430,553 (McKinnie et al. II), Ser. No. 484,338 (McKinnie et al. III), and Ser. No. 551,336 (McKinnie et al. IV), filed Sept. 30, 1982, Apr. 12, 1983, and Nov. 14, 1983, respectively, that (hydrocarbylthio)phenols can be prepared by reacting phenols with hydrocarbyl disulfides in the presence of an aluminum phenoxide catalyst.

SUMMARY OF INVENTION

An object of this invention is to provide a novel process for preparing (hydrocarbylthio)aromatic amines.
Another object is to provide such a process which is adaptable to the preparation of mono- or poly(hydrocarbylthio)aromatic amines.
A further object is to provide such a process which is direct and simple.
These and other objects are attained by reacting an aromatic amine with a hydrocarbyl disulfide so as to form a (hydrocarbylthio)aromatic amine.

DETAILED DESCRIPTION

Aromatic amines utilizable in the practice of the invention include (1) compounds having at least one amino group attached to a carbocyclic or heterocyclic ring of an aromatic compound containing one or more simple and/or fused rings, such as benzene, naphthalene, anthracene, pyrrole, pyridine, indole, etc., rings and (2) reactive heterocyclic amines, such as pyrrole, indole, imidazole, etc. The compounds may bear no substituents other than the required amino group, or they may bear substituents inert to the reaction conditions, such as one or more additional amino groups or substituents such as chloro, fluoro, alkyl, aryl, alkaryl, or aralkyl groups on any positions other than those to be substituted by hydrocarbylthio groups. In the case of coupled aromatic rings, the rings may be directly attached to one another or may be coupled through a bridge such as an oxygen, sulfur, sulfoxide, sulfone, alkyl, or other hydrocarbon link. Useful compounds include, e.g., 4,4'-methylenedianiline, 4-(phenylthio)aniline, 1,3-dimethylpyrrole, 1-methylpyrrole, 2-aminobiphenyl, 4-phenoxyaniline, 7-methylindole, aminobenzenes containing one or two amino groups, such as aniline, 4-butylaniline, 4-methylaniline, 4-chloroaniline, 2-ethylaniline, N-methylaniline, 2,4- and 2,6-diaminotoluenes, 2,6-diamino-1-ethylbenzene, etc.

Hydrocarbyl disulfides which may be reacted with the aromatic amines include saturated and unsaturated aliphatic, cycloaliphatic, and aromatic disulfides in which the hydrocarbyl groups optionally bear inert, such as chloro, substituents. Exemplary of such compounds are methyl, ethyl, propyl, n-butyl, sec-butyl, t-butyl, 2-chloropentyl, cyclopentyl, cyclohexyl, phenyl, benzyl, p-tolyl, and p-chlorophenyl disulfides, etc. This component of the reaction mixture is generally employed in at least the stoichiometric amount required to yield the desired (hydrocarbylthio)aromatic amine, i.e., at least an equimolar amount being used when a mono(hydrocarbylthio)aromatic amine is desired, at least two molar equivalents being utilized when a di(hydrocarbylthio)aromatic amine is desired, etc.

The reaction of the aromatic amine with the hydrocarbyl disulfide is generally conducted at a temperature in the range of about 20°–300° C. and at a pressure of atmospheric up to about 1000 psi in the presence of a catalyst. Suitable catalysts are Lewis acid catalysts, such as metal halides, e.g., aluminum chloride, boron trifluoride, ferric chloride, zinc chloride, etc.; metal alkyls, e.g., triethylaluminum diethylaluminum chloride, ethyl aluminum dichloride, etc.; and the organometallic compounds derived from the reaction of the aromatic amine with the metal halides, metal alkyls, and reactive metals such as aluminum. The preferred catalysts are the metal halides, such as aluminum chloride, boron trifluoride, and boron trichloride. Aluminum chloride is especially preferred. The catalyst is employed in catalytic amounts, generally in a catalyst/aromatic amine mol ratio of about 0.01–0.5/1, preferably about 0.01–0.2/1. When the catalyst is one of the more active catalysts and/or is used in a relatively large amount, the temperature and pressure conditions required are milder than when a less active catalyst and/or a lesser amount of catalyst is utilized. Thus, e.g., when about 0.01–0.1 molar proportion of aluminum chloride is employed, particularly satisfactory results are obtained when the reaction is conducted at about 100°–150° C. and atmospheric pressure, whereas higher temperatures and/or elevated pressures are required for comparable results when aluminum is used instead of aluminum chloride.

In conducting the process of the invention, it is generally preferred to (1) heat a mixture of the catalyst and the aromatic amine at a suitable temperature, usually a temperature higher than the boiling point of the disulfide to be added, e.g., about 100°–150° C., until all of the catalyst has reacted and then (2) heat the reaction mixture at reflux temperature after the disulfide has been added to effect a hydrocarbylthiolation process while removing evolved hydrocarbyl thiol by-product from the reaction vessel. However, it is also satisfactory to conduct the process by simply mixing the catalyst and the reactants together and heating them to the reflux temperature. An inert solvent may be employed if desired but is unnecessary.

The process of the invention results in the formation of (hydrocarbylthio)aromatic amines which are useful as intermediates in the preparation of biologically-active materials, polyurethanes, etc. Some of these amines are novel compounds, e.g., those corresponding to the formulas:

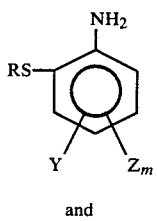

and

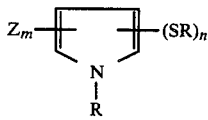

wherein R is a hydrocarbyl group; Y is a hydrocarbylthio group, Z is an inert substituent, i.e., a substituent which is inert to the reaction conditions, such as chloro, fluoro, nitro, amino, hydrocarbyl, or hydrocarbylthio; m has a value of 0–3; and n is an integer of 2–4. The hydrocarbyl groups are preferably alkyl, e.g., methyl, ethyl, etc., groups.

The following examples are given to illustrate the invention and are not intended as a limitation thereof.

EXAMPLE I

A yellow solution of 0.66 mol of aniline and 0.0445 mol of aluminum chloride was stirred at 150° C. for one hour under nitrogen to form a dark solution, which was cooled to 100° C. Then 2.66 mols of methyl disulfide were added, and the reaction mixture was stirred at reflux to a pot temperature of 135° C. The reaction time was 4–5 days. GC analysis of an acid-quenched sample showed 31 area % of methyl disulfide, 6 area % of di(methylthio)aniline, 61 area % of tri(methylthio)aniline, and 2 area % of tetra(methylthio)aniline. The assignments were confirmed by GC/MS.

The reaction mixture was cooled to ambient temperature, and 50.9 g of methyl disulfide were collected by distillation under reduced pressure (40 mm) to a pot temperature of 90° C. The dark blue reaction mixture was diluted with 200 ml of ether, extracted with 100 ml of 1N NaOH, and then two times with 100 ml of saturated aqueous NaCl. The solvent was removed with a rotary evaporator, and the dark blue residue was distilled using a short path still to give 131.6 g (87% yield) of an amber liquid having a boiling point of 120°–185° C. at 0.2–0.3 mm. The bulk of the material distilled at 173° C. GC and NMR analyses indicated that the product was a 74/15/11 mixture of isomeric tri(methylthio)anilines, with 2,4,6-tri(methylthio)aniline being the predominant isomer.

EXAMPLE II

A stirred yellow solution of 0.11 mol of distilled aniline and 0.0075 mol of aluminum chloride was heated in a nitrogen atmosphere to 130° C., at which point a nearly black solution was formed. The solution was cooled to 100° C., 0.11 mol of methyl disulfide was added, and the reaction was stirred at reflux to a pot temperature of 150° C. in about 18 hours. The cooled reaction mixture was diluted with 30 ml of ether, extracted sequentially with 20 ml of 1N NaOH and 20 ml of saturated aqueous NaCl, dried over sodium sulfate, and filtered. The solvent was removed with a rotary evaporator. Distillation at 0.5 mm using a short path still gave a forerun of 3.9 g of aniline (37% recovery) and 6.3 g of a yellow liquid having a boiling point of 60°–110° C. which, analyzed by gas chromatography, showed 86% 4-(methylthio)aniline, 11% 2-(methylthio)aniline, and 3% di(methylthio)aniline.

EXAMPLE III

A mixture of 0.2 mol of 2,4-diaminotoluene and 0.013 mol of aluminum chloride was stirred at 150° C. in a nitrogen atmosphere for 30 minutes and cooled to 100° C. Then 0.3 mol of methyl disulfide was added, and the reaction mixture was stirred at reflux to a pot temperature of 160° C. in about 20 hours. The reaction mixture was cooled, diluted with 100 ml of ether, and treated with 50 ml of 1N NaOH and then with 50 ml of saturated aqueous NaCl. The combined aqueous portions were treated with 25 ml of ether, and the solvent was removed from the combined organic portions under reduced pressure (40 mm) with a rotary evaporator to give 32.6 g of crude product. Analysis by gas chromatography showed 13 area % 2,4-diaminotoluene, 12 area % 3-(methylthio)-2,4-diaminotoluene, 45 area % 5-(methylthio)-2,4-diaminotoluene, and 31 area % 3,5-di(methylthio)-2,4-diaminotoluene.

EXAMPLE IV

A mixture of 0.1 mol of 4-chloroaniline and 0.0067 mol of aluminum chloride was stirred in a nitrogen atmosphere at 150° C. for 30 minutes and cooled to 100° C., and 0.15 mol of methyl disulfide was added. The reaction mixture was then stirred at reflux until a pot temperature of 165° C. was obtained. The reaction mixture was cooled, and 2.66 g of residual methyl disulfide were removed under reduced pressure (40 mm) by distillation to a pot temperature of 90° C. The residue was diluted with 50 ml of ether, treated with 50 ml of 1N NaOH, and then with 50 ml of saturated aqueous NaCl. The ether was removed under reduced pressure with a rotary evaporator to give 17.12 g of crude product. Analysis by gas chromatography showed 2 area % of methyl disulfide, 15 area % 4-chloroaniline, 60 area % 4-chloro-2-(methylthio)aniline, and 19 area % 4-chloro-2,6-di(methylthio)aniline. Distillation through a 6" Vigreux column gave 1.9 g of a forerun of 4-chloroaniline (54%) and 4-chloro-2(methylthio)aniline (b.p. of 44°–80° C. at 0.05 mm), followed by 8.7 g of 4-chloro-2-(methylthio)aniline (93% purity, b.p. of 76°–92° C. at 0.075 mm) and 2.77 g of 4-chloro-2,6-di(methylthio)aniline (79% purity, b.p. of 106°–110° C. at 0.15 mm).

EXAMPLE V

A mixture of 0.1 mol of 4-methylaniline and 0.0067 mol of aluminum chloride was stirred in a nitrogen atmosphere at 150° C. for 30 minutes and cooled to 100° C., and 0.15 mol of methyl disulfide was added. The reaction mixture was then stirred at reflux until a pot temperature of 165° C. was obtained. The residue was diluted with 50 ml of ether, treated with 50 ml of 1N NaOH and then with 50 ml of saturated aqueous NaCl. The ether was removed under reduced pressure with a rotary evaporator to give 17.12 g of crude product. Analysis by gas chromatography showed 14 area % methyl disulfide, 9 area % 4-methylaniline, 56 area % 4-methyl-2-(methylthio)aniline, 17 area % 4-methyl-2,6-di(methylthio)aniline, and 3% others. Distillation through a 6" Vigreux column gave 1.4 g of a forerun of 4-methylaniline (47%) and 4-methyl-2-(methylthio)aniline (53%) having a boiling point of 32°–68° C. at 0.2 mm, followed by 8.4 g of 4-methyl-2-(methylthio)aniline (97% purity, b.p. of 64°–69° C. at 0.15 mm) and 2.8 g of 4-methyl-2,6-di(methylthio)aniline (83% purity, b.p. of 88°–100° C. at 0.15 mm).

EXAMPLE VI

A mixture of 0.093 mol of aniline and 0.007 g-atom of aluminum was stirred at reflux under nitrogen until all of the metal dissolved. The resultant black solution was cooled to 100° C., and 0.1 mol of phenyl disulfide was added. The mixture was heated to 220°–230° C., and 7.76 g of a distillate determined to be a mixture of aniline and thiophenol was collected over five hours. The reaction was cooled, diluted with 15 ml of water, and extracted with 60 ml of ether. The ethereal layer was dried over sodium sulfate and filtered, and the solvent was removed with a rotary evaporator to give 18 g of a dark liquid which solidified upon cooling. GC/MS analysis indicated the composition to be 1 area % of thiophenol, 3 area % of aniline, 13 area % of diphenyl sulfide, 70 area % of diphenyl disulfide, and 13 area % of isomeric (phenylthio)anilines. The isomeric (phenylthio)anilines were isolated by chromatography on silica gel with hexane and then methylene chloride to give a dark liquid analyzing for 11 area % of diphenyl disulfide and 89 area % of a 74/2/13 mixture of 2-, 3-, and 4-(phenylthio)anilines.

EXAMPLE VII

A stirred solution of 0.112 mol of aniline and 0.007 mol of boron trifluoride etherate was heated to 100° C. in a nitrogen atmosphere, and 0.111 mol of methyl disulfide was then added. The reaction mixture was stirred at reflux to a reaction temperature of 133° C. in about five days. The reaction mixture was cooled, and 4.3 g of methyl disulfide were recovered by distillation under reduced pressure (40 mm). The residue was diluted with 50 ml of ether, hydrolyzed with 50 ml of 1N NaOH, and washed with 50 ml of saturated aqueous sodium chloride. Removal of the solvent under reduced pressure gave 11.3 g of a cherry red liquid which was analyzed by gas chromatography and mass spectroscopy to show 68 area % aniline, 7 area % 2-(methylthio)aniline, and 8 area % 4-(methylthio)aniline.

EXAMPLE VIII

A stirred mixture of 0.1 mol of freshly-distilled N-methylaniline and 0.0067 mol of aluminum chloride was heated at 150° C. in a nitrogen atmosphere for 30 minutes. The reaction mixture was cooled to 100° C., 0.15 mol of methyl disulfide was added, and the mixture was heated at reflux to a reaction temperature of 165° C. in about 18 hours. GC analysis showed that 30% of the starting material remained. An additional 0.056 mol of methyl disulfide was added, and the reaction mixture was heated to a reaction temperature of 165° C. in about one hour. The reaction mixture was cooled, and 1.4 g of methyl disulfide was recovered by distillation under reduced pressure (40 mm) to a pot temperature of 80° C. The dark blue residue was diluted with 100 ml of ether, hydrolyzed with 50 ml of 1N NaOH, and the organics then treated with 50 ml of saturated aqueous sodium chloride. Removal of the solvent under reduced pressure with a rotary evaporator gave 14.7 g of crude product which GC/MS analysis showed to contain 13 area % N-methylaniline, 22 area % 2-(methylthio)-N-methylaniline, 33 area % 4-(methylthio)-N-methylaniline, and 24 area % 2,4-di(methylthio)-N-methylaniline.

EXAMPLE IX

A stirred mixture of 0.1 mol of 2-ethylaniline and 0.0067 mol of aluminum chloride was heated at 150° C. in a nitrogen atmosphere for 30 minutes and cooled to 100° C., and 0.15 mol of methyl disulfide was then added. The mixture was heated at reflux until a reaction temperature of 165° C. was achieved. The reaction mixture was cooled to ambient temperature, and 1.65 g of methyl disulfide was recovered by distillation under reduced pressure (40 mm) to a pot temperature of 80° C. The residue was diluted with 50 ml of ether, hydrolyzed with 50 ml of 1N NaOH, and the organics treated with 50 ml of saturated aqueous NaCl. Removal of the solvent with a rotary evaporator under reduced pressure gave 17.4 g of crude product. Distillation through a Vigreux column at 0.15 mm afforded the following:

| Fraction | Wt. (g) | B.P. (°C.) | Composition |
| --- | --- | --- | --- |
| 1 | 1.71 | 40–55 | 98% 2-ethylaniline, 2% 6-(methylthio)-2-ethylaniline |
| 2 | 2.08 | 65–68 | 73% 6-(methylthio)-2-ethylaniline, 26% 4-(methylthio)-2-ethylaniline, 1% 2-ethylaniline |
| 3 | 1.01 | 68–82 | 73% 6-(methylthio)-2-ethylaniline, 27% 4-(methylthio)-2-ethylaniline |
| 4 | 6.57 | 82–102 | 10% 6-(methylthio)-2-ethylaniline, 85% 4-(methylthio)-2-ethylaniline, and 5% 4,6-di(methylthio)-2-ethylaniline |
| 5 | 4.10 | 102–110 | 94% 4,6-di(methylthio)-2-ethylaniline, 5% 4-(methylthio)-2-ethylaniline, 1% unknown |

EXAMPLE X

A stirred mixture of 0.2 mol of 1-methylpyrrole, 0.3 mol of methyl disulfide, and 0.0134 mol of aluminum chloride was heated at reflux temperature in a nitrogen atmosphere for 3.5 hours until a reaction temperature of 135° C. was obtained. The reaction mixture was cooled, and excess methyl disulfide and unreacted 1-methylpyrrole were removed under reduced pressure (40 mm) to a pot temperature of 60° C. The residue was treated with 50 ml of 1N NaOH, diluted with 50 ml of ether, and separated; and the organic layer was extracted with 50 ml of aqueous saturated NaCl. Removal of the solvent with a rotary evaporator gave 21.3 g of product. Analysis by gas chromatography and mass spectroscopy showed 28% of a 20/8 isomeric mixture of (methylthio)-1-methylpyrroles, 40% of a 15/19/5/1 isomeric mixture of di(methylthio)-1-methylpyrroles, and 10% of an 8/2 isomeric mixture of tri(methylthio)-1-methylpyrroles. Distillation through a Vigreux column at 0.1–0.2 mm afforded the following:

| Fraction | Wt. (g) | B.P. (°) | Composition |
| --- | --- | --- | --- |
| 1 | 6.09 | 35–50 | 70 area % 2-(methylthio)-1-methylpyrrole, 25 area % 3-methylthio)-1-methylpyrrole, 4 area % 2,5-di(methylthio)-1-methylpyrrole |
| 2 | 3.87 | 55–65 | 55 area % 2,5-di(methylthio)-1-methylpyrrole, 38 area % 2,3-di(methylthio)-1-methylpyrrole, 5 area % 2,4-di(methylthio)-1-methylpyrrole |
| 3 | 3.15 | 65–66 | 33 area % 2,5-di(methylthio)-1- |

-continued

| Fraction | Wt. (g) | B.P. (°) | Composition |
|---|---|---|---|
| | | | methylpyrrole, 57 area % 2,3-di(methylthio)-1-methylpyrrole, 10 area % 2,4-di(methylthio)-1-methylpyrrole |
| 4 | 1.61 | 66–67 | 8 area % 2,5-di(methylthio)-1-methylpyrrole, 71 area % 2,3-di(methylthio)-1-methylpyrrole, 20 area % 2,4-di(methylthio)-1-methylpyrrole |
| 5 | 3.32 | 67–115 | 8 area % 2,3-di(methylthio)-1-methylpyrrole, 9 area % 2,4-di(methylthio)-1-methylpyrrole, 5 area % 3,4-di(methylthio)-1-methylpyrrole, 65 area % 2,3,5-tri(methylthio)-1-methylpyrrole, 1 area % 2,3,4-tri(methylthio)-1-methylpyrrole |

It is obvious that many variations may be made in the products and processes set forth above without departing from the spirit and scope of this invention.

We claim:

1. A process which comprises reacting a hydrocarbyl disulfide with an aromatic amine having no substituents other than hydrogen on any positions to be substituted by hydrocarbylthio groups in the presence of a catalytic amount of a Lewis acid so as to form a (hydrocarbylthio)aromatic amine.

2. The process of claim 1 wherein the aromatic amine is an aminobenzene.

3. The process of claim 2 wherein the aminobenzene is aniline.

4. The process of claim 2 wherein the aminobenzene is a diaminobenzene.

5. The process of claim 1 wherein the aromatic amine is a heterocyclic amine.

6. The process of claim 5 wherein the heterocyclic amine is 1-methylpyrrole.

7. The process of claim 1 wherein the hydrocarbyl disulfide is an alkyl disulfide.

8. The process of claim 7 wherein the alkyl disulfide is methyl disulfide.

9. The process of claim 1 wherein the hydrocarbyl disulfide is an aryl disulfide.

10. The process of claim 9 wherein the aryl disulfide is phenyl disulfide.

11. The process of claim 1 wherein the Lewis acid is aluminum chloride.

* * * * *